United States Patent
Bogart et al.

[11] Patent Number: 5,889,255
[45] Date of Patent: Mar. 30, 1999

[54] METHOD OF DEBURRING EYELENS NEEDLE BLANKS WITH A LASER BEAM

[75] Inventors: Michael W. Bogart, Milford; Michael S. Kassim, Monroe, both of Conn.

[73] Assignee: United States Surgical Corporation, Norwalk, Conn.

[21] Appl. No.: 949,444

[22] Filed: Oct. 14, 1997

[51] Int. Cl.$^6$ ................................................. B23K 26/00
[52] U.S. Cl. ............................... 219/121.65; 219/121.66; 219/121.83; 219/121.85
[58] Field of Search ...................... 219/121.65, 121.66, 219/121.68, 121.69, 121.82, 121.83, 121.85; 163/1, 4, 5; 606/223

[56] References Cited

U.S. PATENT DOCUMENTS

| | | |
|---|---|---|
| 1,757,129 | 5/1930 | McClure . |
| 2,023,807 | 12/1935 | Gruss et al. . |
| 3,850,011 | 11/1974 | Shepard et al. . |
| 3,998,259 | 12/1976 | Zocher . |
| 4,100,393 | 7/1978 | Luther . |
| 4,159,686 | 7/1979 | Heim . |
| 4,182,341 | 1/1980 | Perri . |
| 4,458,614 | 7/1984 | Iwashita . |
| 4,608,480 | 8/1986 | Bizot et al. . |
| 4,700,043 | 10/1987 | Matsutani . |
| 4,818,834 | 4/1989 | Rupert . |
| 4,910,377 | 3/1990 | Matsutani et al. ............. 219/121.83 X |
| 5,012,066 | 4/1991 | Matsutani et al. ................. 219/121.68 |
| 5,043,553 | 8/1991 | Corfe et al. . |
| 5,344,412 | 9/1994 | Wendell et al. . |
| 5,345,057 | 9/1994 | Muller . |
| 5,371,338 | 12/1994 | Proto et al. . |
| 5,378,137 | 1/1995 | Asakawa et al. . |
| 5,384,945 | 1/1995 | Spingler . |
| 5,453,595 | 9/1995 | Proto et al. . |
| 5,479,980 | 1/1996 | Spingler . |
| 5,515,871 | 5/1996 | Bittner et al. ........................... 128/898 |
| 5,585,017 | 12/1996 | James et al. . |

FOREIGN PATENT DOCUMENTS

| 2-52189 | 2/1990 | Japan ................................ 219/121.71 |
|---|---|---|

*Primary Examiner*—Gregory L Mills

[57] ABSTRACT

A method of removing edges from an eyeless operating needle blank includes the steps of providing needle blanks having an end portion which defines a bore. Aligning the end portion, which defines a bore, longitudinally with a laser. The laser is fired such that radiation from the laser is incident on the end portion. The incident radiation from the laser forms rounded edges about the end portion.

7 Claims, 3 Drawing Sheets

METHOD OF DEBURRING EYELENS NEEDLE BLANKS WITH A LASER BEAM

BACKGROUND

1. Technical Field

This disclosure relates to a method of removing edges on the end of an eyeless operating needle blank and, more particularly, to using a laser to remove the edges on the proximal end of eyeless surgical needle blanks.

2. Background of the Related Art

An eyeless operating needle blank has a proximal end portion with a bore formed therein of a predetermined depth extending along the axis of the needle blank. An end of a suture is inserted into the bore and, subsequently, the end portion is staked, to attach the suture to the needle blank. Opposite the proximal end portion is a distal tip portion for piercing soft tissue.

Many techniques exist for forming the bore in the end portion of the needle blank, such as, drilling machine, electric discharge machining, electron beam machining, laser beam machining, etc. These machining processes may leave nonconformities at the inside and outside diameters of the bore. In needle blanks with small outside diameters the wall of the needle blank defined between the bore and the outside diameter is very thin and can be very sharp. The sharp edges on the inside diameter of the needle blank can cause the suture to rupture and break away from the needle blank prematurely, i.e., when the needle blank is bent relative to the suture. Sharp edges or burrs on the end of the needle blank can also be created on the outside diameter during manufacture (i.e., cutting the needle blanks to length). These sharp edges or burrs result in rejection during the needle blank inspection process.

Sharp edges or burrs can be eliminated by breaking the edges on the inside and outside diameters at the entrance of the bore. Heim, U.S. Pat. No. 4,159,686, teaches a method for smoothing the eye of a needle blank. The method includes using a laser beam to round out edges, however the techniques disclosed are for use in sewing needle blanks which define an eye substantially perpendicular to the needle blank's axis. Wendell, U.S. Pat. No. 5,344,412, teaches laser machining for catheters. The catheters have side ports laser machined substantially perpendicular to the longitudinal axis of the catheter.

U.S. Pat. Nos. 5,371,338 to Proto and Buchter, 5,384,945 to Spingler, 5,453,595 to Proto and Buchter and 5,479,980 to Proto, all incorporated herein by reference, disclose devices for creating needle blanks and drilling bores into the ends of the needle blanks. Wire from a spool is tensioned, cleaned and straightened. The wire is manipulated and aligned along its longitudinal axis with a laser beam. The distance from the laser beam and the alignment of the work piece with respect to the laser are precisely arranged. The laser drills a hole into the end portion of the wire and the wire is cut to length to create a needle blank with a bore for a suture. The bore is created by a laser beam aligned with the needle blank along its longitudinal axis. It would be advantageous to introduce an edge removing technique after the operation of drilling the bore. The prior art teaches that laser machining be done at an angle with the longitudinal axis of the needle blank. This would require realignment and refocus of the laser beam if longitudinal alignment is required to drill the bore. This would be time consuming and difficult to incorporate into the process.

Therefore, a need exists for incorporating a laser process which can provide a rounded edge to both the inside and outside diameters of the suture end of an eyeless needle blank. It would be advantageous to be able to maintain the laser beam along the longitudinal axis of the needle blank in order to round out the edges of the bore. It is also desirable to be able to use the drilling laser for creating both the bore and for rounding its edges.

SUMMARY

A method of removing edges from an eyeless operating needle blank includes the steps of providing needle blanks having an end portion which defines a bore. The end portion, which defines a bore, is aligned longitudinally with a laser. The laser is fired such that radiation from the laser is incident on the end portion. The incident radiation from the laser forms rounded edges about the end portion.

BRIEF DESCRIPTION OF THE DRAWINGS

Various embodiments of the subject apparatus are described herein with reference to the drawings wherein.

DETAILED DESCRIPTION OF PREFERRED EMBODIMENTS

The following disclosure presents a novel method for removing sharp edges and burrs on the inside and outside diameters of an end portion of an eyeless needle blank. The sharp edges or burrs are removed by filing a laser beam longitudinally at the end portion having a suture bore. This creates a melted region at the edges of the end portion. The melted region creates a chamfer or radius. Hence making the eyeless operating needle blank more suitable for use.

Figure 1:
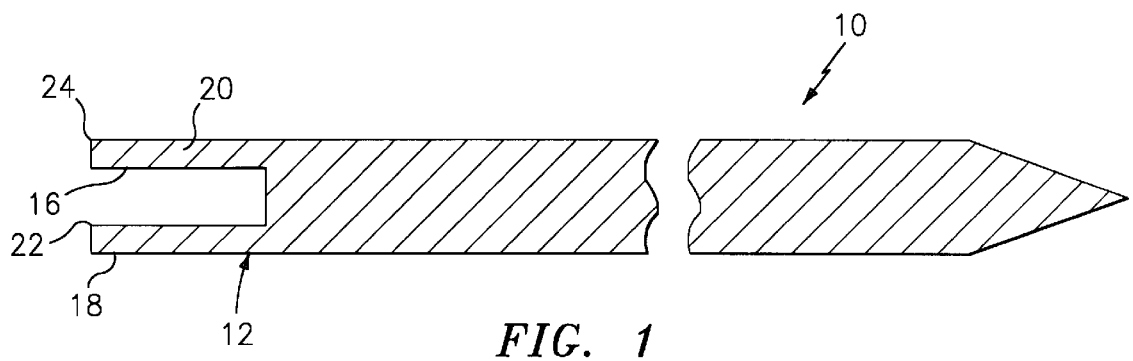
FIG. 1 is a cross section of an eyeless operating needle blank.

Referring now in specific detail to the drawings in which like reference numerals identify similar or identical elements throughout the several views, and initially to FIG. 1, one embodiment of an eyeless operating needle blank 10 is shown before applying the technique described herein. Eyeless needle blank 10 has an end portion 12 which defines a longitudinal bore. The bore created in end portion 12 may be machined by a laser beam. Generally, a $CO_2$, eximer or Nd:YAG laser can be used to form the bore. Once the bore is machined, a side wall 20 is formed maintaining substantially a uniform thickness. Side wall 20 has an inner surface 16 and an outer surface 18. Inner surface 16 forms and edge 22 at the end of end portion 12. Outer surface 18 forms edge 24 at the end of end portion 12. Edges 22 and 24 may contain burrs or sharp edges due to the processing or machining. Eyeless needle blank 10 is generally made from stainless steel, preferably 455 grade.

Figure 2A:
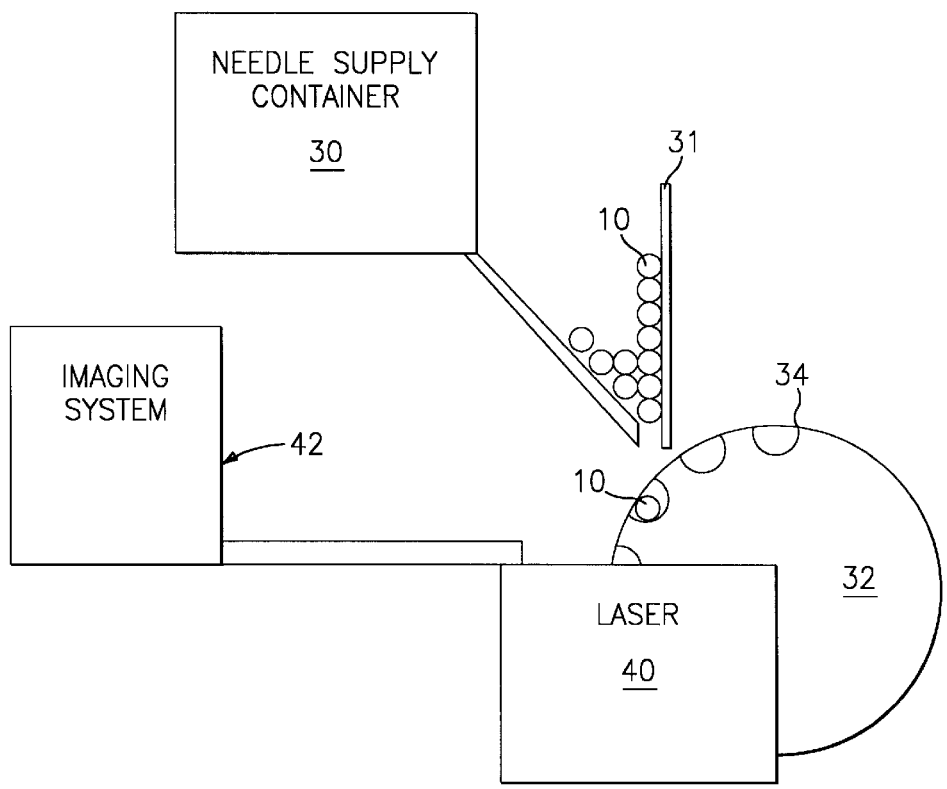
FIG. 2A is a schematic front view of an apparatus for removing edges from an eyeless operating needle blank.
Figure 2B:
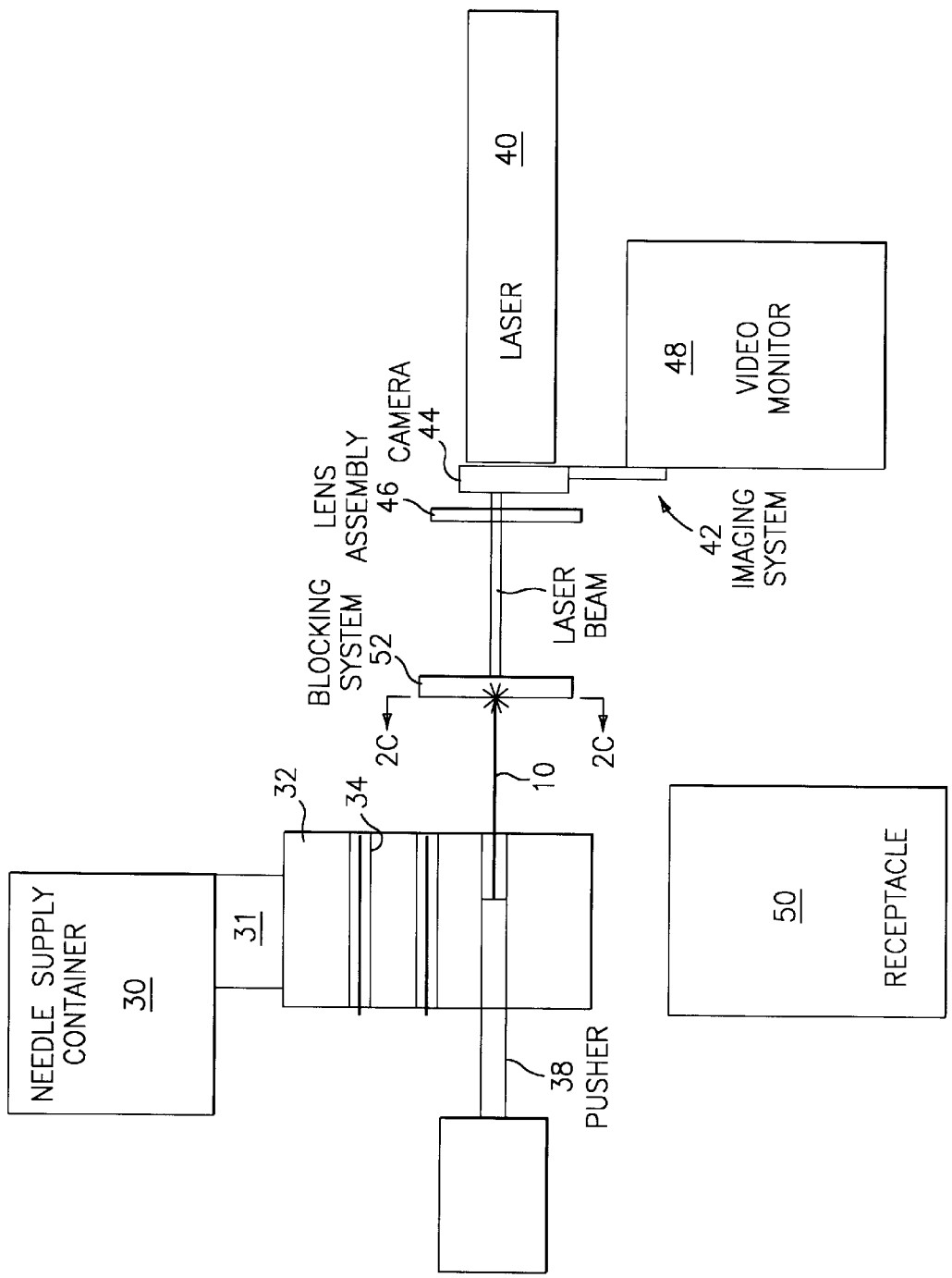
FIG. 2B is a schematic side view of the apparatus for removing edges from eyeless operating needle blank blanks.

Referring now to FIG. 2A, eyeless needle blank 10 is processed to remove sharp spots or burrs on edges 22 and 24. Eyeless needle blank 10 is placed in a supply container 30 and supplied to a drum 32 having a plurality of troughs 34 about its circumference by a supply hopper 31. Each trough 34 is dimensioned to receive eyeless needle blank 10. Drum 32 rotates maintaining eyeless needle blank 10 in a fixed position. As shown in FIG. 2B, when drum 32 reaches a predetermined location, eyeless needle blank 10 is aligned along its longitudinal axis with a laser 40 such that when laser 40 is activated a laser beam falls incident on end portion 12.

Alignment of end portion 12 which is closest to laser 40 may be assisted by an imaging system 42. Imaging system 42 generally includes a video camera 44, a lens assembly 46 and a video monitor 48. In a preferred embodiment, lens assembly 46 contains both a focal lens of laser 40 and a focal lens for video camera 44.

Figure 2C:
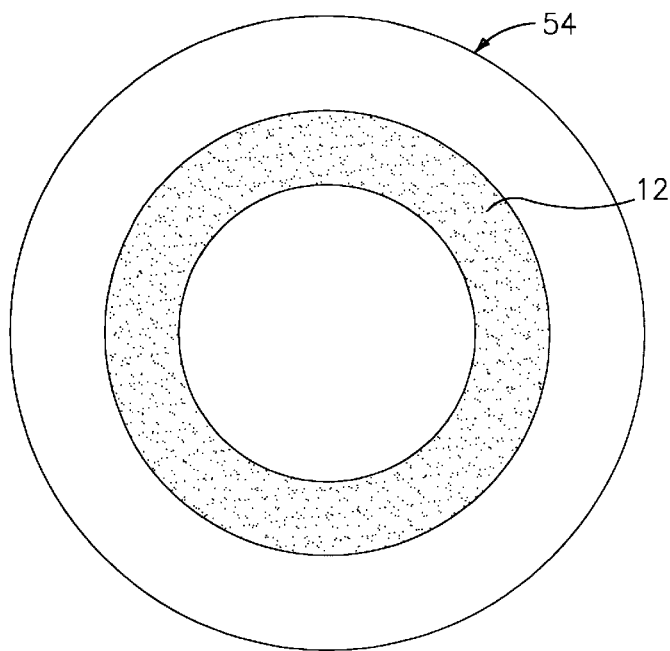
FIG. 2C is an enlarged section view of the needle blank end portion and the laser spot.

A pusher 38 moves eyeless needle blank 10 longitudinally toward laser 40 until a predetermined distance is achieved. One method of achieving the appropriate distance is having a blocking system 52 prevent translation beyond the maximum allowable distance. Blocking system 52 can be removed prior to firing laser 40. This distance corresponds to the appropriate focal distance from laser 40. That is, the point at which the laser 40 can provide the requisite amount of energy to the end portion 12 to remove sharp edges and burrs. If a Nd:YAG laser is used the focal distance from the lens of laser 40 may be between 2.5 inches and 3.5 inches, preferably between 2.75 inches and 3.25 inches. Eyeless needle blank 10 is irradiated by light from laser 40. The amount of energy used can be between 0.08 joules and 1.10 joules, with a preferred range between 0.10 joules and 0.90 joules and preferably about 0.45 joules. The amount of laser exposure time can range between 0.1 seconds and 0.6 seconds with a preferred range between 0.1 seconds and 0.6 seconds. A preferred spot size 54 for the laser beam, i.e. the area irradiated at the end portion, is between 0.020 inches and 0.080 inches, preferably about 0.054 inches. See FIG. 2C. This achieves sufficient incident energy to cause melting of the edges 22 and 24 without damaging side wall 20. The laser parameters can be adjusted to allow for varying needle blank sizes, varying bore sizes and varying materials selected for the needle blanks. It is also preferred to fire a single laser shot at each eyeless needle blank 10.

Figure 3:
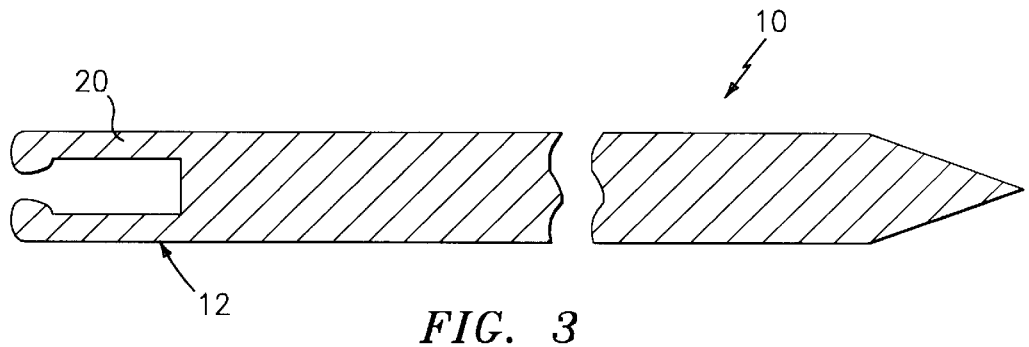
FIG. 3 is a cross section of an eyeless needle blank after multiple laser shots.

FIG. 3 shows a rejected needle. When excessive power is deposited, side wall 20 begins to close radially inward. This is not desirable since sutures will not be capable of entering the bore.

Before irradiation by laser 40 is performed, an optical inspection step can be performed by imaging system 42 and can be used to ensure that an eyeless needle blank is within trough 34 and also to check if eyeless needle blank 10 has a bore formed within it. Imaging system 42 generates an image which can be compared to a reference to determine if a needle blank is present and if present whether the needle blank has a bore. This additional step prevents laser 40 from firing when it is unnecessary. This additional step can also be used to improve the quality of the process by identifying needle blank blanks that need to be removed.

After irradiation by laser 40, pusher 38 retracts pulling assembly 10 back into its position prior to alignment with laser 40. Drum 32 rotates further and assembly 10 is allowed to fall out of trough 34. Eyeless needle blank 10 is captured by a receptacle 50. Assembly 10 is guided to other locations for further processing.

Figure 4:
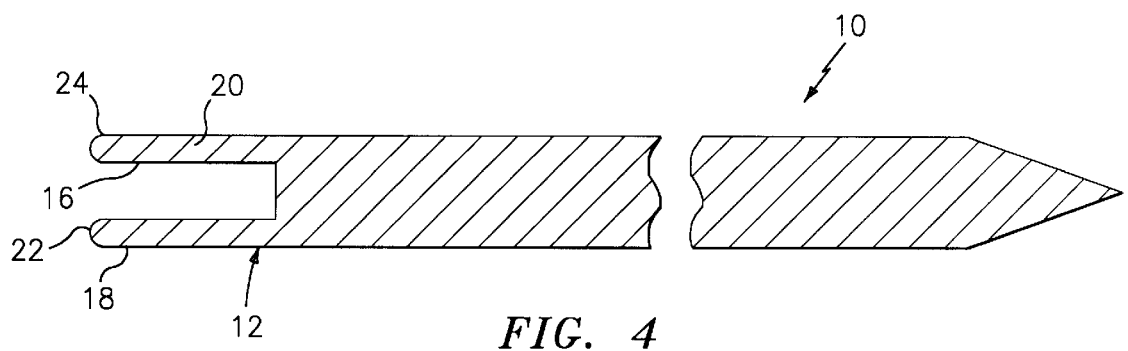
FIG. 4 is a cross section of an eyeless operating needle blank after sharp edges and burrs are removed.

Referring to FIG. 4, a cross section of assembly 10 is shown after laser irradiation. Edges 22 and 24 are rounded and any sharp corners and burrs are removed as a result of the incident laser radiation.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A method of deburring eyeless needle blanks comprising the steps of:
   providing at least one eyeless needle blank having a longitudinal bore extending from an end of the needle blank;
   providing a drum having a circumferential peripheral surface and at least one trough extending longitudinally along the circumferential peripheral surface;
   providing a laser capable of emitting a laser beam of sufficient power to anneal the end of the needle blank;
   positioning the needle lengthwise within the trough;
   rotating the drum to a position in which the needle blank is coaxially aligned with the laser beam;
   moving the needle blank such that the end of the needle blank abuts a surface of a blocking member positioned with respect to the focal point of the laser beam;
   removing the blocking member from the path of the laser beam; and
   firing the laser such that the laser beam is directed onto the end of the needle blank for a period of time sufficient to deburr the end of the needle.

2. The method of claim 1 further including the steps of:
   retracting the needle blank after the laser has been fired;
   rotating the drum to a position wherein the deburred needle blank is allowed to exit the trough; and
   collecting the deburred needle blank.

3. The method of claim 1 further including the step of monitoring the needle blank with an imaging system.

4. The method of claim 1 wherein laser beam power from about 0.80 joules to about 1.10 joules is directed onto the end of the needle blank for a period of time sufficient to deburr the end of the needle.

5. An annealing system for deburring eyeless of needle blanks which comprises:
   a reservoir of eyeless needle blanks;
   a rotatable drum having a circumferential peripheral surface and at least one trough extending longitudinally along the circumferential peripheral surface, the trough being shaped so as to receive an eyeless needle blank from the reservoir, the rotatable drum being positionable wherein the trough is aligned with a laser capable of emitting a laser beam of sufficient power to anneal an end of the needle blank;
   a blocking member having a needle abutment surface, the blocking member being movable between a first position wherein the needle abutment surface is positioned with respect to a focal point of the laser beam, and a second position wherein the abutment surface is out of alignment with the laser beam; and
   a needle pusher for advancing the needle blank such that the end of the needle abuts the needle abutment surface of the blocking member when the blocking member is in the first position.

6. The annealing system of claim 5 further including a video imaging system for monitoring the position of the eyeless needle blank.

7. The annealing system of claim 6 further including a receptacle for the collection of deburred eyeless needle blanks.

\* \* \* \* \*